United States Patent
Campbell et al.

(10) Patent No.: US 7,192,400 B2
(45) Date of Patent: Mar. 20, 2007

(54) DEVICE AND METHOD FOR VASCULAR MONITORING

(75) Inventors: Michael K. Campbell, Hoover, AL (US); William F. Kuester, III, Blaine, MN (US); Daniel L. Mooradian, Eagan, MN (US)

(73) Assignee: Synovis Life Technologies, Inc., St. Paul, MN (US)

( * ) Notice: Subject to any disclaimer, the term of this patent is extended or adjusted under 35 U.S.C. 154(b) by 0 days.

(21) Appl. No.: 10/279,751

(22) Filed: Oct. 24, 2002

(65) Prior Publication Data

US 2004/0082868 A1    Apr. 29, 2004

(51) Int. Cl.
*A61B 5/00* (2006.01)
*A61B 5/02* (2006.01)

(52) U.S. Cl. ........................ 600/486; 600/505
(58) Field of Classification Search ............... 600/486, 600/488, 504–505, 549, 561
See application file for complete search history.

(56) References Cited

U.S. PATENT DOCUMENTS

| | | | |
|---|---|---|---|
| 3,623,473 A | 11/1971 | Andersen et al. ........... 128/2 R |
| 4,419,999 A | 12/1983 | May, Jr. et al. ............. 128/691 |
| 4,607,637 A | 8/1986 | Berggren et al. ........ 128/334 C |
| 4,624,257 A | 11/1986 | Berggren et al. ........ 128/334 C |
| 4,729,366 A | 3/1988 | Schaefer ..................... 128/1.6 |
| 4,903,502 A | 2/1990 | Hanson et al. .............. 62/228.5 |
| 4,917,090 A | 4/1990 | Berggren et al. ........... 606/153 |
| 4,917,091 A * | 4/1990 | Berggren et al. ........... 606/153 |
| 4,997,439 A | 3/1991 | Chen ........................... 606/216 |
| 5,036,868 A | 8/1991 | Berggren et al. ............ 128/898 |
| 5,089,008 A | 2/1992 | Chen ........................... 606/216 |
| 5,123,908 A | 6/1992 | Chen ........................... 606/153 |
| 5,207,226 A | 5/1993 | Bailin et al. ............. 128/661.08 |
| 5,250,057 A | 10/1993 | Chen ........................... 606/153 |
| 5,289,821 A * | 3/1994 | Swartz ........................ 600/455 |
| 5,323,789 A | 6/1994 | Berggren et al. ............ 128/898 |
| 5,336,233 A | 8/1994 | Chen ........................... 606/153 |
| 5,588,436 A * | 12/1996 | Narayanan et al. ......... 600/459 |
| 6,077,227 A * | 6/2000 | Miesel et al. ................ 600/486 |
| 6,277,078 B1 * | 8/2001 | Porat et al. .................. 600/486 |

OTHER PUBLICATIONS

"Instructions for Use: Cook-Swartz Doppler Flow Probe and Monitoring System", 1998 Cook Vascular Incorporated FM-15588 Aug. 1999.

* cited by examiner

*Primary Examiner*—Robert L. Nasser
(74) *Attorney, Agent, or Firm*—Fredrikson & Byron, PA

(57) ABSTRACT

A vascular coupler adapted to be fixed into position upon a blood vessel and there retain and position a matable sensing device. In a preferred embodiment, the vascular coupler is an anastomotic coupler and the sensing device comprises an ultrasonic Doppler probe.

27 Claims, 10 Drawing Sheets

SECTION A-A

DEVICE AND METHOD FOR VASCULAR MONITORING

FIELD OF THE INVENTION

This invention relates generally to medical devices, and more particularly to devices for monitoring parameters such as blood flow in a blood vessel during or after a surgical procedure. In another aspect, the invention relates to medical devices that can be attached to vessels within the body, including anastomotic devices for the secure attachment of vessel portions to each other.

BACKGROUND OF THE INVENTION

Over the last decades, many advances have been made in the area of microvascular surgery, particularly in the area of free flap tissue surgery. Free flaps are regularly used in plastic and reconstructive surgery, for example in breast reconstruction. In free flap surgery, tissue and/or muscle is removed from one part of the body, along with an associated artery and vein, and is reattached to another part of the body. The artery and vein of the transferred tissue and/or muscle are then anastomosed (that is, connected) to a native artery and vein in order to achieve blood circulation in the transferred tissue and/or muscle.

The anastomosis of the free flap tissue to the native tissue is typically done using microvascular techniques, including under microscopic visualization. In previous years, several surgical instruments and techniques have been developed to aid in anastomosis. One known system for creating an anastomosis is the Ventrica MVP™ System. This system includes two pairs of elliptical magnets and a delivery device. One pair of magnets is deployed to form the anastomotic port within the graft vessel. The other pair is deployed to form an identical anastomotic port within a target vessel. The graft vessel port is placed onto the target vessel to form the anastomosis.

Another known system is the JOMED SOLEM Graft-Connector, a system consisting of a connector, a handle and a combined delivery and expansion activation unit. The connector is a T-shaped connector with a self-expanding stent inside the main body. The delivery handle has two L-shape holders and a center pin. The L-shaped holder facilitates insertion of the connector into a coronary artery. Once in place, release of the holder and expansion of the connector inside the artery is activated by pulling out the central needle and its cap. The self-expanding stent anchors the connector in the coronary artery without the need to suture.

A yet another known system is an anastomosis coupler, described in Applicant's own U.S. Pat. Nos. 4,607,637; 4,624,257; 4,917,090; and 4,917,091, the disclosures of which are incorporated herein by reference. This anastomotic coupler is a surgical instrument that allows a surgeon to more easily and effectively join together two blood vessel ends. A coupler of the type described is in commercial use under the tradename Microvascular Anastomotic Coupler System. It can be seen from the product literature that the coupler involves the use of two fastener portions, in the shape of rings, upon which are secured respective sections of the vessel to be attached. Each fastener portion is also provided with a series of pins, and corresponding holes for receiving those pins, in order to close and connect the portions, and in turn the vessel, together.

While free flap surgeries have a history of success, highly undesirable consequences of a flap failure still remain a possibility. One of the main causes of flap failure is a lack of blood being supplied to the flap tissue. Things that commonly disturb circulation in a flap include vascular occlusion, hemorrhage, or infection. When not enough blood is supplied to the flap tissue, tissue necrosis results. However, if it can be recognized early enough that the flap is not receiving adequate circulation, it may be saved, or salvaged. The window of time for salvaging the flap after a lack of blood flow is recognized is very small. It is therefore critical that any lack of blood flow in a transferred flap be quickly recognized.

Handheld Doppler probes are available and used by surgeons to assess vascular flow prior to or during such surgical procedures. See, for instance, the intraoperative doppler probes produced by company such as Vascular Technology, Inc. Such probes are typically permanently positioned on the distal tip of a pen-like device, rather than themselves be placed or left within the body.

Certain post-operative monitoring techniques are also used for assessing blood flow in a free flap tissue. One technique involves the use of a device such as the Cook-Swartz Doppler Flow Probe and Monitor System (see Instructions for Use by COOK Vascular™ Incorporated). This product is described as being useful for assessing vascular patency. An implantable 20 MHz ultrasonic probe properly aligned in a suturable cuff, which provides direct vessel monitoring of microvascular anastomoses at a specific site along a designated vessel. The absence of the monitor's audible signal alerts the medical staff that a potential problem with perfusion may exist, thus providing the opportunity for early intervention.

The product literature goes to describe it as a 1 mm piezoelectric crystal that is placed directly on the vessel to provide a means of monitoring flow with specificity of vessel origin (in-situ 3-7 days). When vessel monitoring is completed, the probe may be removed by applying minimal traction, leaving only the cuff in-situ. A troubleshooting protocol including cable and channel verifiers, along with an internal self test circuit in monitor, is said to allow for patient assessment. The cuff itself (which is said to be patented) secures the crystal to the vessel in proper alignment. Retention tabs are provided for strain relief, in an attempt to reduce the chance of accidental crystal dislodgement. Battery operation allows portability for monitoring at any location. Unfortunately, devices such as that described above continue to suffer from various drawbacks, including in particular the fact that the probe itself is in an approximate position that is less than optimal (approximately 90 degrees to the flow of blood). Moreover, the position of both the cuff, and in turn the probe itself, is unpredictable and itself subject to change, e.g., as the cuff moves along and/or around the vessel, or even when the patient himself changes positions.

See also U.S. Pat. No. 5,588,436 to Narayanan et al., which provides what appears to be an intravascular application of Doppler monitoring. The '436 patent describes the manner in which the use of Doppler involves monitoring blood flow following vessel anastomosis as a part of organ transplant, reconstructive surgery, and other procedures where small vessels must be reattached and can frequently close off following surgery. Instruments developed for this purpose have involved securing the Doppler transducer head to the vessel, such as with a cuff, then closing the incision with the conductor wires exiting the patient where they are attached to an appropriate ultrasound frequency generator, back-scattering sensor, and control computer.

The '436 patent goes on to provide what it describes as ultrasonic Doppler probe that can be introduced intracranially and manipulated to the desired configuration for traversing the natural spaces, i.e., the ventricles and cisterns, of the brain to measure blood flow at a particular site upon a cerebral vessel to help determine whether an aneurysm has been successfully treated. The probe includes means 22 said to be used in fixing the orientation of the operative surface with respect to at least one longitudinal axis of the sheath, or to the distal ends of the electrically conductive wires.

It can be seen, therefore, that while Doppler probes are helpful in blood flow monitoring, they suffer from several drawbacks. One drawback with implanted probes arises in the present inability to reliably and stably position the probe either within or about a vessel. A probe must be positioned securely about a blood vessel so that a transducer will be properly oriented to receive consistent signals from that blood vessel. Surgeons often report difficulties in positioning the probe because they must manually position the probe about the vessel with their hands or with forceps. Positioning the probe is also problematic because of the restricted space in the body in which the surgeon has to work. These problems of positioning also increase the risk that the probe would be accidentally detached from the blood vessel and lost in the body. Accordingly, there remains a need for a device and method that will enable a surgeon to position a probe about a blood vessel with more consistency and greater ease.

SUMMARY OF THE INVENTION

Figure 1:
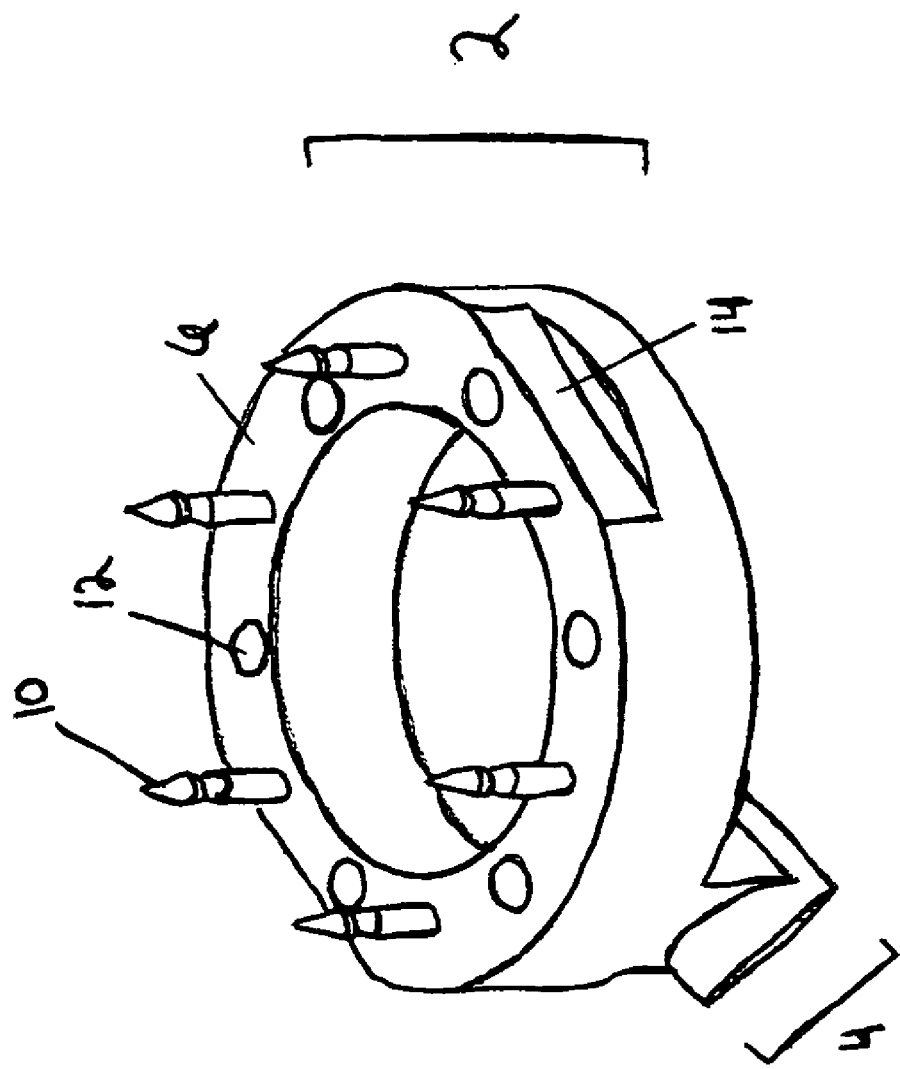
FIG. 1 is a perspective view of a fastener according to a preferred embodiment of the invention.
Figure 2:
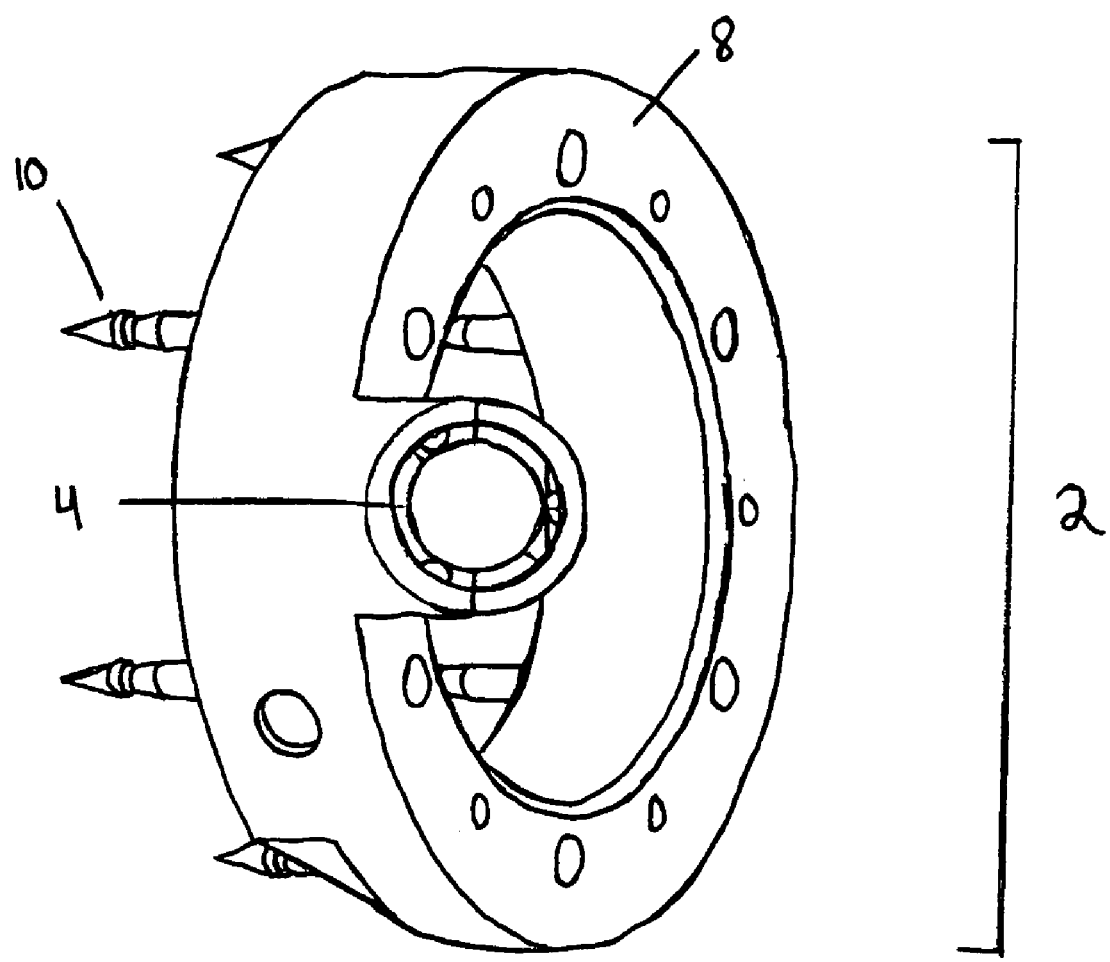
FIG. 2 is another perspective view of the fastener depicted in FIG. 1.
Figure 3:
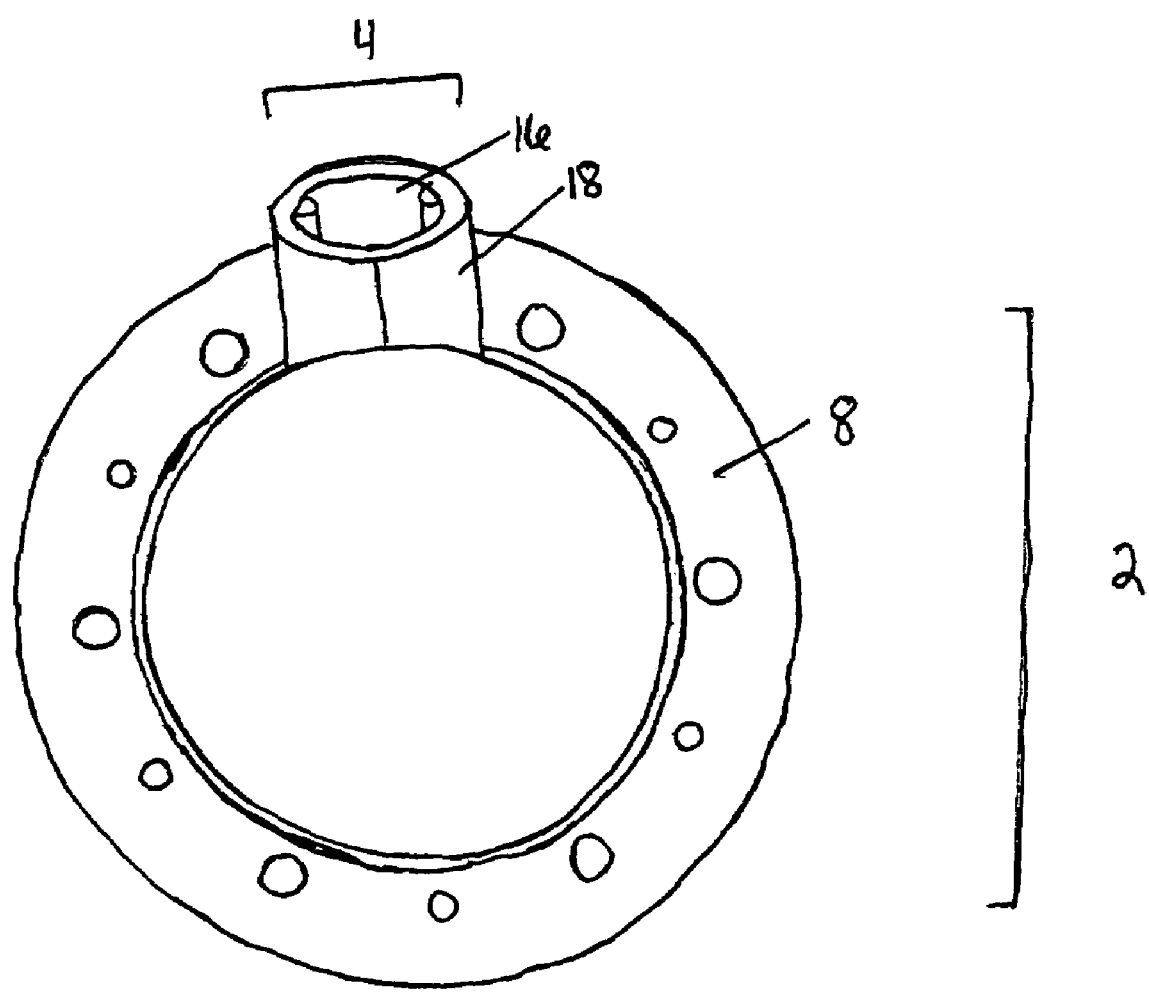
FIG. 3 is a bottom view of the lower surface of the fastener depicted in FIG. 1.

The present invention includes a vascular coupler adapted to be fixed into position upon a blood vessel and there retain and position one or more sensing devices in a predetermined manner (e.g., position and orientation). The sensing devices, in turn, can be used to monitor or evaluate one or more parameters associated with recovery and success of the surgical procedure. The vascular coupler can be of relatively large dimensions (e.g., diameter) as used for coronary and other procedures, or of relatively smaller dimensions, as used for microvascular procedures.

In one embodiment, the coupler is adapted to receive one or more of the sensing devices once the coupler itself has been positioned within the body. In the same, or optional, embodiment, one or more fastener portions forming the coupler are provided with one or more sensing devices, or components thereof, prior to being positioned within the body.

A coupler suitable for use in this invention can be provided in the form of a single component (for example, a suitably modified form of the JOMED-SOLEM GraftConnector), or a plurality of components (for example, suitably modified forms of the magnets of the Ventrica MVP™ System or the fasteners of the Microvascular Anastomotic Coupler System), and can be coupled to the vessel in that it will be used to either join one or more vessel portions, and/or to be positioned upon, around and/or within a vessel.

In a preferred embodiment, the vascular coupler is an anastomotic coupler adapted to join two or more portions of a vessel together, and the sensing device(s) comprise an ultrasonic Doppler probe. In an even more preferred embodiment, the anastomotic coupler is a coupler of substantially the type described in U.S. Pat. Nos. 4,607,637, 4,624,257, 4,917,090 and 4,917,091, the disclosures of which are incorporated herein by reference, which has been suitably modified to receive and retain a corresponding sensing device.

A preferred anastomotic coupler of this type generally comprises two identical fastener portions adapted to be connected together by the surgeon and under microscopic visualization in order to join abutting vascular portions. The fastener portions can be preloaded into a delivery device, adapted to connect the portions in situ in order to provide a secure anastomotic attachment. Either or both of the fastener portions are adapted to receive a corresponding sensing device, as in the form of a Doppler probe releasably positioned upon a suitable delivery instrument. The use of identical portions in this manner, provides the surgeon with the option to use either or both portions for the placement of a sensing device, and facilitates both the manufacture and use of the coupler itself.

In the embodiment in which the combination of coupler and sensing device is made in situ, it is preferred that one or more of the fastener portions be provided with one or more mating portions, e.g., receptacles, adapted to be mated with a corresponding portion, e.g., probe, of a respective sensing device. The dimensions and geometry of the fastener portions, and in turn of the coupler itself, can be selected by the surgeon. This, in turn, permits the surgeon to position and use the corresponding sensing device(s) in a manner that is considerably more stable and predictable than those previously taught.

In a preferred embodiment, for instance, the sensing device comprises a conventional Doppler probe which can be used 'as is' or is preferably suitably modified (e.g., dimensioned and/or shaped) to permit it to be mated within a receptacle of a fastener portion in order to form a combination device of this invention. A receptacle can be adapted to position the sensing device upon the coupler, and in turn with respect to the vessel, in any suitable orientation and manner. In a particularly preferred embodiment, the receptacle and probe are configured in a manner that facilitates both the initial placement of the probe in the receptacle, e.g., using an insertion tool as described herein, as well as the later removal of the probe from the receptacle (e.g., by the use of minimal pulling forces), and in turn, from the body itself.

In yet another embodiment, the invention provides a fastener portion for use in forming a vascular coupler and having a receptacle for attaching a sensing device in a fixed position and/or geometry.

The invention further provides a method of making a coupler, sensing device (including optional delivery instrument), and combination as described herein, as well a kit or adaptors for retrofitting a conventional coupler and/or conventional sensing device in order to provide them with suitable mating means for each other.

In another embodiment, the present invention may be provided as a kit, the kit including a coupler and a sensing device such as a Doppler probe, the sensing device either being provided in position within the coupler, or separately provided, for example with or within an insertion tool. An insertion tool of the type described herein is considered to be novel in its own right, in that it permits the releasable delivery of a probe to a vascular site.

DETAILED DESCRIPTION

The invention further provides a method of preparing and a method of using a coupler and sensing device combination of the type disclosed, including a system that includes either a coupler and/or sensing device adapted to be positioned together, as well as various other components, such as an insertion tool adapted to position the sensing device within the coupler.

The predictable, and predetermined orientation of a sensing device, as permitted by the combination device, permits a variety of new methods and opportunities in the course of its use. For instance, in a particularly preferred embodiment, a combination of this invention is particularly well suited to permit the Doppler sensing device to perform a technique referred to herein as "flow/velocity trend analysis", in which various aspects concerning blood flow within a vessel can be monitored and recorded in order to provide a baseline for objective comparison with later-collected data. That baseline can be provided in either absolute terms, e.g., in terms of volume per unit time and/or in relative terms, as by comparing the flow and/or velocity within the particular vessel at various points over time (e.g., hours or days) or with units or thresholds unique to and calibrated within the instrument itself. For this purpose, those skilled in the art will appreciate the manner in which a zero-crossing technique which generates a signal that is roughly proportional to the Doppler shift frequency and also to the blood velocity is particularly well suited.

The preferred coupler of this invention provides a unique advantage over Doppler probes previously used, in that it permits the probe to be reliably positioned in a manner that provides a fixed geometry (including angle with respect to blood flow) as well as a fixed and uniform cross section, corresponding to the inner diameter of the coupler itself. These features, in turn, permit the recordation, evaluation and manipulation of data over time and varying conditions, and permit also the calculation of related kinetics and flow characteristics (including blood flow and velocity).

The ability to predictably and stably position a Doppler probe, in this manner, reduces many or all of the variables encountered with conventional devices. Since anastomotic failures tend to be rather abrupt, the ability to continually and reliably monitor and compare blood flow can be used to generate and send signals associated with the detection of failure events.

The present invention will be further described with reference to the Drawing, which provides various figures showing a preferred vascular coupler adapted to be fixed into position upon a blood vessel and there retain and position a sensing device. A preferred embodiment of a fastener component of a vascular coupler used in this invention is illustrated in FIGS. 1–5. In this embodiment, the vascular coupler is an anastomotic coupler of the type described in U.S. Pat. Nos. 4,607,637, 4,624,257, 4,917,090, and 4,917,091. The coupler comprises two identical fasteners adapted to be connected together as one coupler system. While in this embodiment the fasteners are identical, one with skill in the art should recognize that fasteners of any configuration, whether identical or not, can be used as long as they are adapted to be connected together. Each fastener is further provided with a receptacle, which is configured to receive a sensing device. The receptacle may be oriented about each fastener in any angle suitable for the sensing device to receive readings from a blood vessel.

Figure 4:
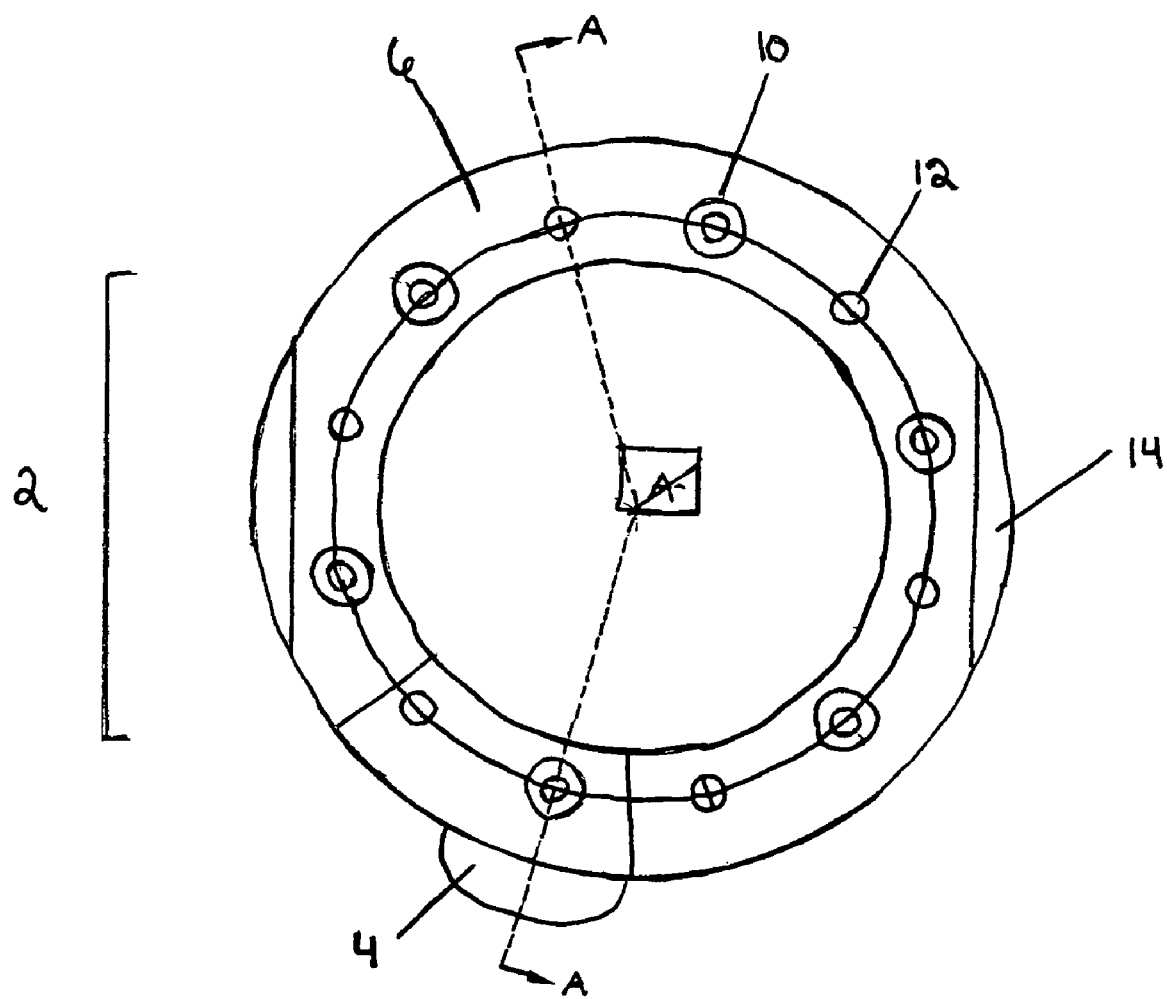
FIG. 4 is a top view of the upper surface of the fastener depicted in FIG. 1.

FIGS. 1–5 show a preferred fastener 2 having a ring shape. However, it should be apparent to one with skill in the art that the fastener may be made into any suitable shape. The fastener 2 comprises an upper surface 6 and a lower surface 8 which are plane-parallel. FIGS. 1 and 4 display the upper surface 6, which contains a number of axially directed pins 10 and intermediate holes 12 distributed on a circumference around the center of the fastener 2 and extending through the upper surface 6. The upper surface 6 of the fastener 2 may optionally include a shoulder 14.

FIG. 4 displays the lower surface 8 of the fastener 2, also showing a receptacle 4. Preferably, the receptacle 4 extends through the lower surface 8. In the preferred embodiment, the receptacle 4 is oriented about the lower surface 8 in order to maintain a sensing device at a predetermined manner, including predetermined distance and angle with respect to the longitudinal axis of the fastener 2. An even more preferred embodiment is shown in FIG. 5, wherein the receptacle 4 is oriented about the lower surface 8 in order to maintain a sensing device at an angle 30 degrees in a through-the coupler orientation with respect to the longitudinal axis of the fastener 2.

Figure 5:
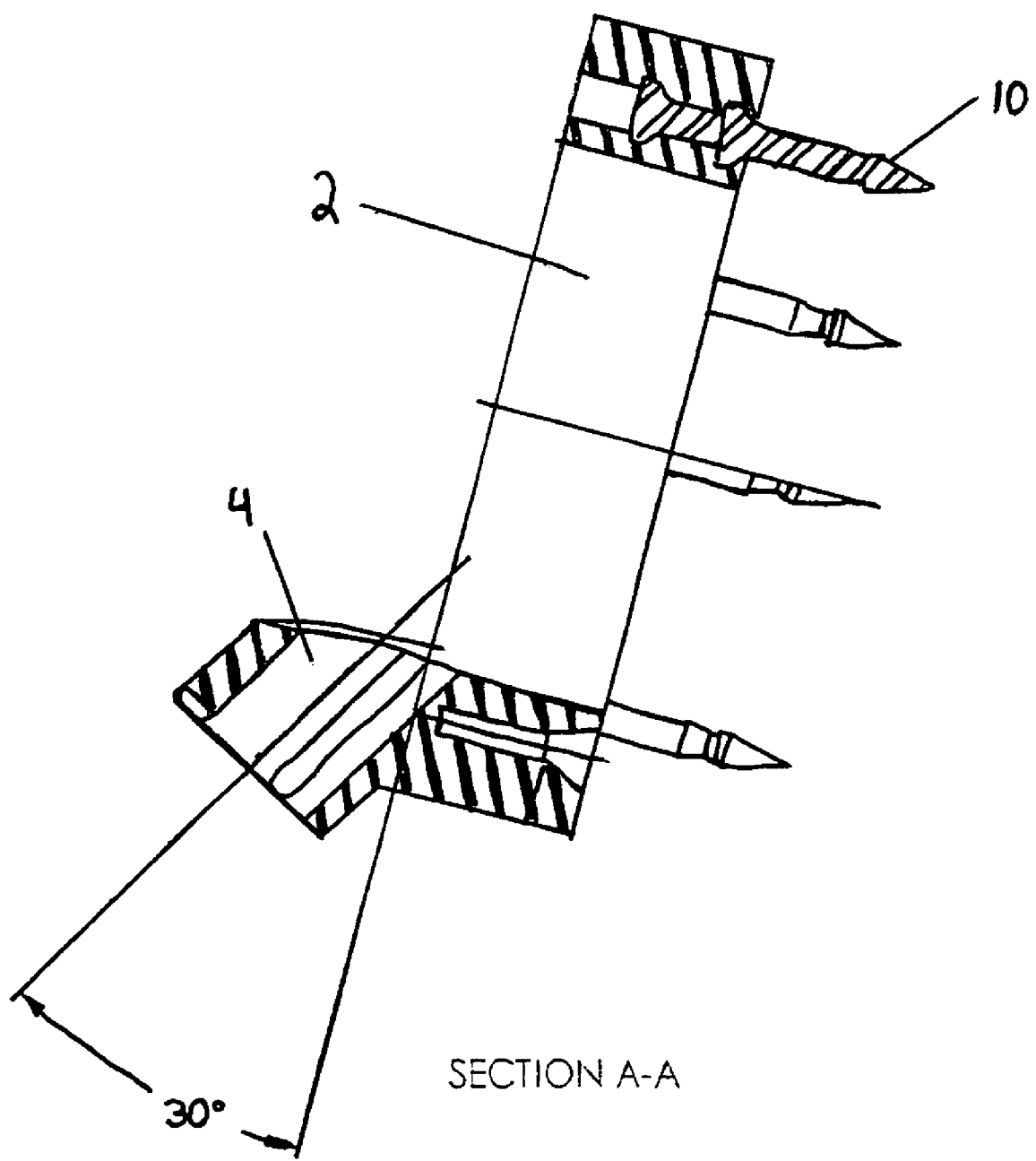
FIG. 5 is a cross-sectional view of the fastener taken from Section A—A of FIG. 4.
Figure 8:
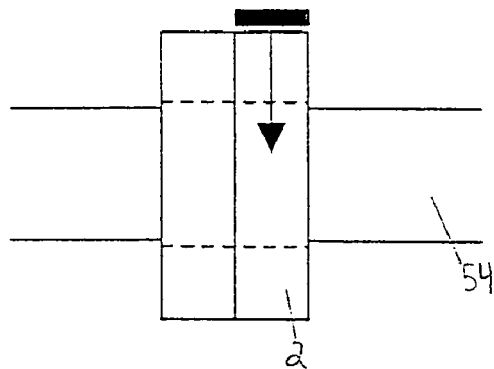
FIG. 8 shows a sensing device oriented about a coupler in a ninety degree angle through-the-coupler orientation.
Figure 9:
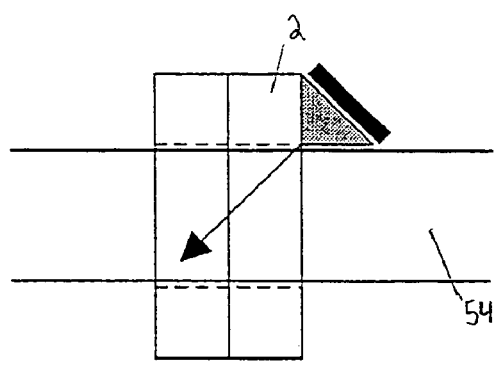
FIG. 9 shows a sensing device oriented about a coupler in a forty-five degree through-the-coupler orientation.
Figure 10:
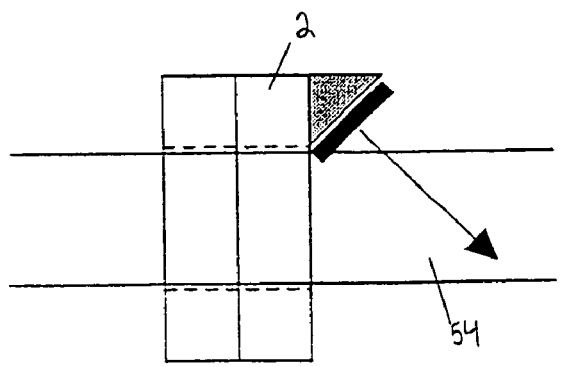
FIG. 10 shows a sensing device oriented about a coupler in a forty-five degree beyond-the-coupler orientation.

While in the preferred embodiment, as shown in FIG. 5, the sensing device is maintained at an angle 30 degrees in a through-the-coupler orientation with respect to the longitudinal axis of the fastener 2, it should be apparent to those preferred in the art that other suitable orientations and angles may be used. FIGS. 8 through 10 display other possible orientations of the sensing device. In FIG. 8, the sensing device is positioned about one of the fasteners at a 90 degree angle with respect to the longitudinal axis of the fastener in a through-the-coupler orientation. In FIG. 9, the sensing device is positioned about one of the fasteners at a 45 degree angle with respect to the longitudinal axis of the fastener in a through-the-coupler orientation. In FIG. 10, the sensing device is positioned about one of the fasteners at a 45 degree angle with respect to the longitudinal axis of the fastener in a beyond-the-coupler orientation. With regard to the through-the-coupler orientations, the sensing device monitors blood flow in the area of the vessel that is in between the coupler. With regard to the beyond-the-coupler orientation, the sensing device monitors blood flow in the area of the vessel that is directly outside of the coupler, either upstream or downstream.

Figure 6:
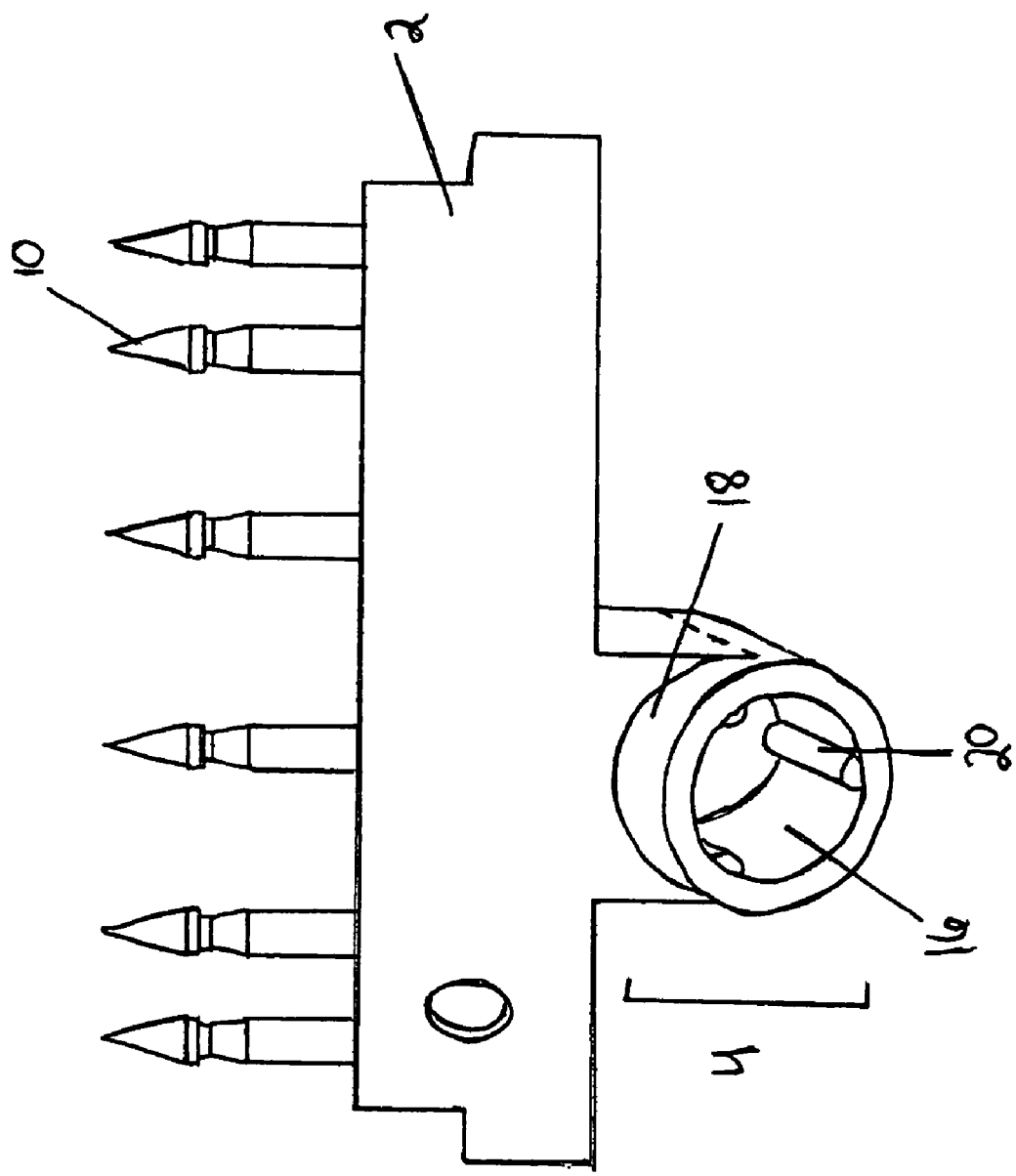
FIG. 6 is a front view of a receptacle according to a preferred embodiment of the invention.
Figure 7:
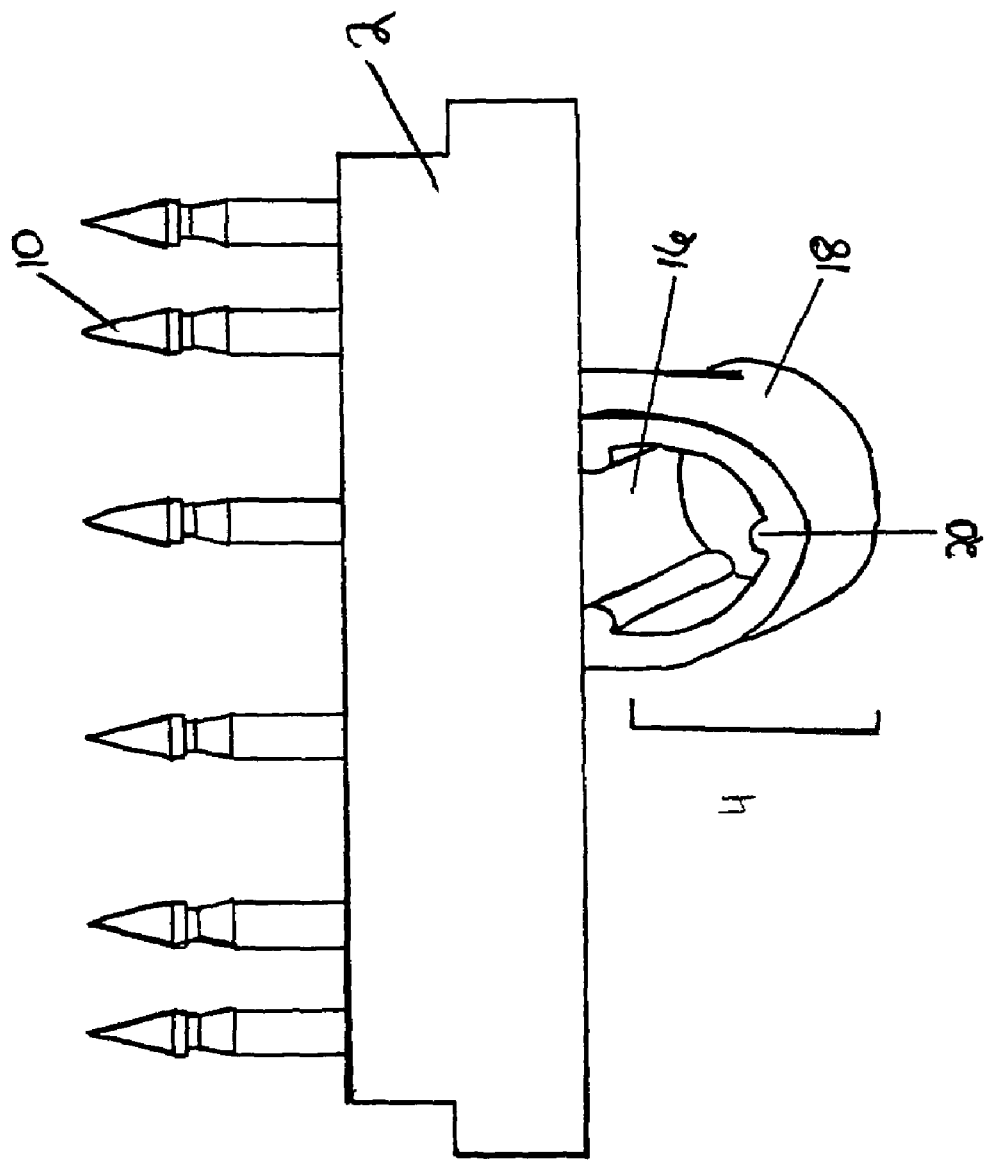
FIG. 7 is a rear view of a receptacle according to the embodiment depicted in FIG. 6.

In the preferred embodiment, the sensing device is inserted into the receptacle 4 and held into place by friction. The receptacle 4 has an internal surface 16 and an external surface 18. The internal surface 16 of the receptacle 4 may be configured in any manner suitable to hold a sensing device by friction. FIG. 6 is a front view of the receptacle 4 displaying the internal surface 16 configured as a circular shape and also having one or more rod members 20 oriented in a latitudinal direction about the internal surface 16 of the receptacle 4 in order to provide a friction fit when a circular shaped sensing device is inserted into. FIG. 7 is a rear view of the receptacle 4 shown in FIG. 6, also showing the rod members 20 oriented latitudinally. While in the preferred embodiment, the receptacle 4 is configured as a circular shape, it should be apparent to one of skill in the art that any suitable shape may be used to obtain a friction fit. While in these embodiments, three rod members are shown, it should be apparent to one with skill in the art than any number of suitable rod members may be used. Further, the rod members may be resilient in order to provide more cushioning and friction to retain a sensing device.

While in the preferred embodiment, a sensing device is secured about a fastener by the use of a receptacle providing a friction fit, several other methods of securing a sensing device to the fastener may be used. In one alternative method, the sensing device can be mounted to the fastener using a silicone adhesive or any other suitable alternative. Modifications to the mounting surfaces of the fastener may also be made to improve adhesion. For example, the mounting surface may be roughened to create additional texture that improves adhesion. In another example, a cavity may be created within the fastener so the sensing device may be placed inside of and this increases the bonding surface area and improves retention. In another method of securing the sensing device, the sensing device may be attached to the fastener using molded clips or by using a mechanical latch and pin mechanism.

The sensing device may be secured to the coupler before or after the anastomosis is created. In a preferred embodiment, the sensing device is secured to the coupler after the anastomosis is created. In the preferred embodiment, the coupler comprises two fasteners connected together, and a surgeon will typically secure the sensing device to only one of the two fasteners. Both fasteners are equally adapted to receive a sensing device so a surgeon may adapt the procedure of securing a sensing device to a fastener to external circumstances of the surgery. For example, a surgeon may choose a particular fastener based on whether he is right handed or left handed. A surgeon may also choose a fastener based on the circumstances within the surgical site, for example based on which side the free flap is located.

Figure 11:
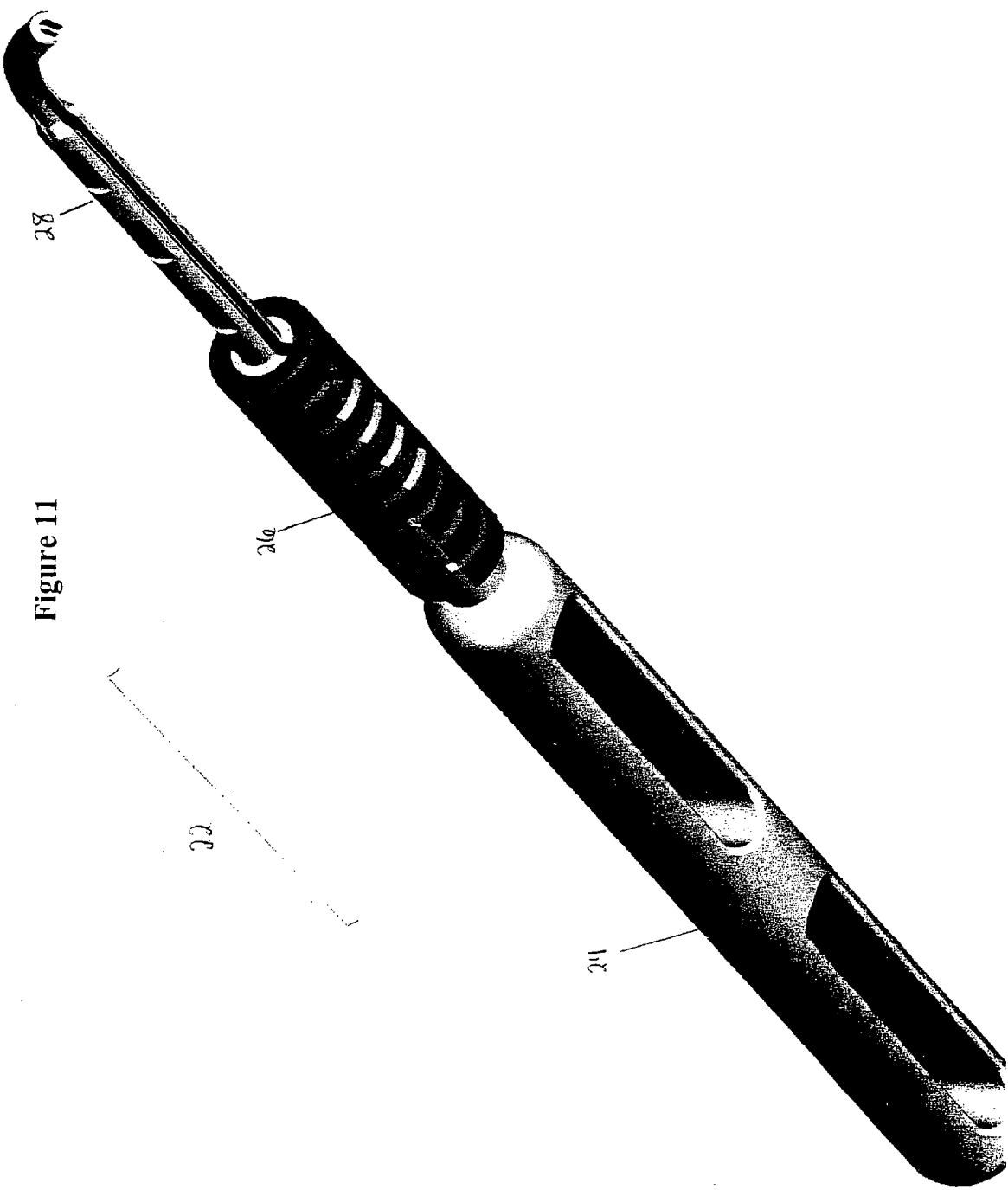
FIG. 11 shows an insertion tool according to a preferred embodiment of the invention.

In a more preferred embodiment, the sensing device is inserted into a receptacle of one of the fasteners of the coupler. When inserting the sensing device into the receptacle on a fastener, the surgeon may use any suitable method. In the preferred embodiment, the sensing device is inserted into the receptacle using an insertion tool. FIG. 11 displays a preferred insertion tool 22 of the present invention. The insertion tool 22 comprises a handle portion 24, a pushing member 26, and a tip portion 28. In a preferred embodiment, the tip portion 28 is bent in shape. In a more preferred embodiment, the tip portion 28 is bent at a forty-five degree angle. The insertion tool is beneficial because it makes it easier for the surgeon to mount the sensing device to the fastener. It is also beneficial because it allows a surgeon to test the whether the sensing device actually works before actually inserting it into a receptacle.

Preferably, the insertion tool retains the sensing device with enough force to reduce the probability of accidental release of the sensing device. It is preferred that the insertion tool/sensing device retention force be less than the sensing device/fastener retention force so that it will be ensured that the sensing device will remain mounted to the fastener while being detached from the insertion tool. The delivery of the sensing device can be facilitated by the use of various release or ejection features associated with the insertion tool.

In another embodiment, the sensing device is secured to the coupler before an anastomosis is created. In this embodiment, the coupler comprises two unconnected fasteners. The sensing device may be secured to the coupler according to any of the above methods or one or both of the fasteners may come pre-loaded with the sensing device already attached. In this embodiment, the coupler is pre-loaded with the sensing device in a manner so the sensing device does not interfere with the normal usage of the coupler.

In yet another embodiment, the present invention may be provided as a kit, the kit including a coupler and a sensing device, the sensing device either being provided pre-loaded in position within the coupler, or separately provided, for example with or within an insertion tool.

Figure 12:
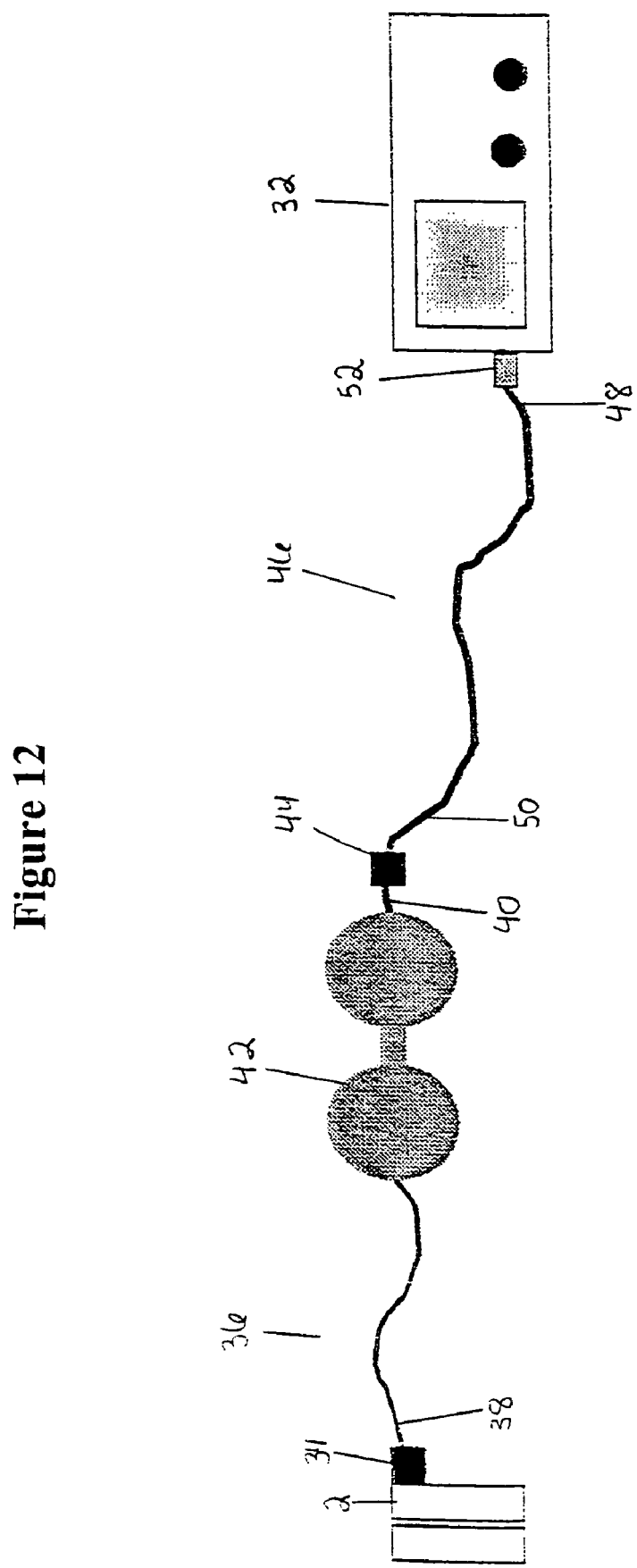
FIG. 12 is an illustration of a probe system and monitor according to a preferred embodiment of the invention.

The sensing device of this invention may be any probe capable of intra-operative or post-operative detection, assessment and/or monitoring of tissue viability, metabolic function and/or blood flow in surgical procedures such as microvascular anastomosis. In a preferred embodiment, the probe may be an ultrasonic Doppler probe. In a more preferred embodiment, the probe is a multi-component system consisting of a transducer, percutaneous lead, external lead, mounting pad for attachment to the patient and associated connectors. The probe system is also attached to a monitor. FIG. 12 shows a complete multi-component probe system 30 along with an attached monitor 32. As shown, a transducer 34 is connected to one of the fasteners. Any transducer suitable for ultrasonic Doppler monitoring may be used. In a preferred embodiment, the transducer is made of an approved implantable material such as HDPE or silicone. In a more preferred embodiment, the transducer comprises a piezoelectric crystal. Also, the transducer may be any size conforming to the dimensions of a receptacle used on the fastener of an anastomotic coupler. For example, a circular transducer is suitable to be received by a receptacle having its internal surface circular in shape. Preferably, the transducer is a circular piezoelectric crystal being between about 0.5 mm to about 1 mm in size.

The transducer 34 will also have a percutaneous lead 36 attached to its surface. The percutaneous lead 36 has a proximal end 38 and a distal end 40. The percutaneous lead 36 preferably comprises two wires insulated by a common insulating material. The wires may be any wires suitable for monitoring 20 MHz signals from the transducer. Also, the insulating materials preferably comprise biocompatible materials, for example class VI medical grade materials.

At the proximal end 38, the percutaneous lead 36 will have one wire attached to each surface of the transducer 34. When manufacturing, any method of attaching these two wires to each surface of the transducer may be used in order to produce a strong conductive bond with the transducer itself. Suitable methods include but are not limited to soldering, friction bonding, adhesive bonding, or attaching the lead during the manufacturing of the transducer. In addition, the bond between the transducer and the two wires must be strong enough to allow for separation of the probe from the receptacles of the fastener by simply pulling on the lead itself. After its use, the transducer may either be left inside of the body within a receptacle, or it may be removed, e.g., by applying enough force to the percutaneous lead so as to pull the transducer from the receptacle, and to then pull the lead through the skin and to the surface of the body. In a preferred embodiment, the strength of the bond between the transducer 34 and the percutaneous lead 36 is greater than a force necessary to remove the transducer 34 from the patient by applying a mechanical force to the percutaneous lead 36.

The distal end 40 of the percutaneous lead 36 is shown as being positioned within an optional bonding pad 42 that is placed on the human skin. The bonding pad 42 is composed of medical grade material suitable for contact with human skin, for example USP grade V or VI material. A variety of alternative approaches can be used to attach the lead to the skin, including for instance the use of patches and sutures. The bonding pad 42 is attached to the skin in such a way that the force necessary to remove the pad from the skin must be greater than the force necessary to separate the percutaneous lead 36 from an external lead 46. In a preferred embodiment, the force necessary to disconnect the percutaneous lead 36 from the external lead 46 should be less than the force necessary to remove the bonding pad 42 from the skin.

The very end of the distal end 40 of the percutaneous lead 36 is fitted with a first connector 44 that allows it to be further connected to a proximal end 50 of an external lead 46. The external lead 46 is composed of any wire suitable for use in carrying signals and is insulated with materials suitable for skin contact. Preferably, the lead is adapted to carry a 20 MHz signal.

Preferably, the first connector 44 is a medical grade electrical connector. In one embodiment, the first connector 44 is a non-locking connector. In a more preferred embodiment, the first connector 44 is an electrical medical grade connector. Non-locking connectors are beneficial in reducing the probability of accidental removal of the transducer from the anastomosis site. That is, if the external lead 46 is accidentally tugged on, the non-locking connector 44 will cause it to disconnect from the percutaneous lead 36 without disturbing the transducer 34. The bonding pad 42 will also help to prevent the transducer 34 from being disturbed.

A distal end 48 of the external lead 46 is finally connected to a monitor 32. It may be connected in any suitable manner. In a preferred embodiment, the lead 46 is connected using a second connector 52, which may be of the same type as the first connector 44. The monitor 32 generates a signal which is sent to the transducer 34 and is transmitted through the vessel site. The transducer 34 then detects the signal transmitted through the vessel and sends this back to the monitor 32, which converts the signals into a form that can be read by the user. For example, the signals may be converted to sound or to a visual display or both. Any monitor/probe combination capable of detecting audio output frequency and blood flow velocity may be used. Preferably the combination is capable of detecting audio output frequency in the range of about 80 to about 3000 Hz and blood flow velocity in the range of 0.5 cm/sec to about 15 cm/sec.

In a preferred embodiment, the monitor 32 displays a visual numeric value representing the frequency shift of the Doppler signal. The use of a numeric value allows the surgeons to store and trend numbers over time in order to detect and analyze patterns. Optionally, these numbers may also be downloaded into computer software for further analysis. In another preferred embodiment, the monitor 32 allows for monitoring of at least two anastomosis sites. In this embodiments, the monitor 32 has one or more Doppler probe inputs and is capable of user selectable monitoring of either channel. Further, while the preferred multi-component probe system uses leads to connect the probe to the monitor, a wireless system may also be used wherein the probe is configured to communicate with the monitor without the use of leads. This system would be particularly advantageous should a surgeon desire to leave the probe inside of the body at the anastomosis site.

The coupler of this invention can be used in combination with sensing devices, or components thereof, for a variety of uses. For example, it may be adapted to indicate or measure one or more blood flow parameters, oxygen, temperature, pH, or the presence or concentration of one or more biochemical compounds, of glucose, oxygen levels, as well as blood flow using Doppler techniques.

Similarly, a coupler of the type described herein can be used as a platform, including a self-contained platform, to provide some or all of the various components needed to perform a particular sensing activity. For instance, various energy and data sources, as well as micro-circuitry components and micro-electromechanical systems (referred to as MEMS and BioMEMS), can be provided in reduced size and positioned upon or within the coupler surface, including a transmitter adapted to send related signals to a monitoring unit positioned elsewhere.

What is claimed is:

1. A combination comprising a vascular coupler adapted to be fixed into position upon a blood vessel and there retain and position one or more sensing devices in a predetermined position and orientation, and one or more sensing devices, wherein the coupler is an anastomotic coupler formed by the connection of a pair of matching fastener portions, either or both of which is provided with a receptacle for receiving one of the one or more sensing devices and wherein at least one sensing device is removably retained within the receptacle.

2. A combination according to claim 1 wherein the combination of the coupler and the one or more sensing devices is adapted to be made once the coupler itself has been positioned within the body.

3. A combination according to claim 1 wherein the combination of the coupler and the one or more sensing devices is adapted to be made outside the body.

4. A combination according to claim 1 wherein at least one of the fastener portions is mated, or adapted to be mated, with at least one of the one or more sensing devices.

5. A combination according to claim 1 wherein at least one of the one or more sensing devices include a device, or component thereof adapted to indicate or measure one or more blood flow parameters, oxygen, temperature, pH, or the presence or concentration of one or more biochemical compounds.

6. A combination according to claim 1 wherein the fastener portions are identical portions, adapted to be connected by the use of axially directed pins and corresponding intermediate holes.

7. A combination according to claim 6 wherein at least one of the one or more sensing devices comprises an ultrasonic Doppler probe adapted to be releasably positioned within and retained by the receptacle of either fastener portion under microscopic visualization.

8. A combination according to claim 7 wherein the Doppler probe comprises a circular piezoelectric crystal.

9. A method of monitoring or evaluating a tissue site following vascular surgery, comprising the steps of providing and using a combination according to claim 1.

10. A method according to claim 9 wherein the combination of the coupler and the one or more sensing devices is made once the coupler itself has been positioned within the body.

11. A method according to claim 9 wherein the combination of the coupler and the one or more sensing devices is made outside the body.

12. A method according to claim 9 wherein at least one of the fastener portions is mated, or adapted to be mated, with at least one of the one or more sensing devices.

13. A method according to claim 9 wherein at least one of the one or more sensing devices include a device, or component thereof, adapted to indicate or measure one or more blood flow parameters, oxygen, temperature, pH, or the presence or concentration of one or more biochemical compounds.

14. A method according to claim 9 wherein the fastener portions are identical portions, adapted to be connected by the use of axially directed pins and corresponding intermediate holes.

15. A method according to claim 14 wherein at least one of the one or more sensing devices comprises an ultrasonic Doppler probe adapted to be releasably positioned within and retained by the receptacle of either fastener portion under microscopic visualization.

16. A method according to claim 15 wherein the Doppler probe comprises a circular piezoelectric crystal.

17. A method of monitoring one or more parameters following vascular surgery, comprising the steps of providing and positioning a combination of the coupler and one or more sensing devices according to claim 1.

18. A method according to claim 17 wherein the combination of the coupler and the one or more sensing devices is made once the coupler itself has been positioned within the body.

19. A method according to claim 17 wherein the combination of the coupler and the one or more sensing devices is made outside the body.

20. A method according to claim 17 wherein at least one of the one or more sensing devices include a device, or component thereof, adapted to indicate or measure one or more blood flow parameters, oxygen, temperature, pH, or the presence or concentration of one or more biochemical compounds.

21. A method according to claim 17 wherein at least one of the one or more sensing devices comprises an ultrasonic Doppler probe adapted to be releasably positioned within and retained by the receptacle of either fastener portion under microscopic visualization.

22. A method according to claim 21 wherein the Doppler probe comprises a circular piezoelectric crystal.

23. A combination comprising a vascular coupler and one or more sensing devices, wherein the coupler is an anastomotic coupler formed by the connection of a pair of matching fastener portions, either or both of which is provided with a receptacle for receiving a sensing device comprising an ultrasonic Doppler probe, the probe being removably retained within the receptacle at a predetermined distance and angle with respect to the longitudinal axis of the coupler and at the anastomotic site.

24. A combination according to claim 23 wherein the rings comprise, respectively, a series of pins, and corresponding holes for receiving those pins, the pins and holes being adapted to close and connect the portions, in the course of forming an anastomotic joint.

25. A combination according to claim 23 wherein the predetermined angle is selected from the group consisting of 30, 45 and 90 degree angles with respect to the longitudinal axis.

26. A combination according to claim 23 wherein the sensing device is removably retained within the receptacle by the use of friction fit, mechanical means, or adhesive.

27. A combination according to claim 23 wherein the receptacle is adapted to permit the sensing device to be later removed from the receptacle and from the body itself.

* * * * *